United States Patent [19]

Cardinali et al.

[11] Patent Number: 6,025,431
[45] Date of Patent: Feb. 15, 2000

[54] THICKENED PERSONAL CARE COMPOSITION

[75] Inventors: Martin S. Cardinali, Martinsville, N.J.; Daniel W. Verstrat, Ooltewah, Tenn.

[73] Assignee: National Starch and Chemical Investment Holding Corporation, Wilmington, Del.

[21] Appl. No.: 08/819,462

[22] Filed: Mar. 17, 1997

Related U.S. Application Data

[63] Continuation-in-part of application No. 08/698,690, Aug. 16, 1996.

[51] Int. Cl.$^7$ .................................................. C08L 41/00
[52] U.S. Cl. ...................... 524/547; 524/17; 524/156; 524/277; 524/388; 524/548; 524/555; 524/556; 524/558; 524/560; 524/561
[58] Field of Search ..................... 524/765, 767, 524/17, 156, 277, 388, 547, 548, 555, 556, 558, 560, 561

[56] References Cited

U.S. PATENT DOCUMENTS

| Re. 33,156 | 1/1990 | Shay et al. ............................ 526/301 |
| 4,012,437 | 3/1977 | Shachat et al. ...................... 260/482 R |
| 4,128,520 | 12/1978 | Barabas et al. ......................... 524/824 |
| 4,616,074 | 10/1986 | Ruffner ................................. 526/318 |
| 4,806,345 | 2/1989 | Bhattacharyya ........................ 424/70 |
| 4,892,916 | 1/1990 | Hawe et al. ............................ 526/304 |
| 5,011,987 | 4/1991 | Barron et al. ........................... 560/221 |
| 5,164,177 | 11/1992 | Bhatt et al. ............................... 424/47 |
| 5,238,992 | 8/1993 | Outubuddin et al. ................... 524/755 |
| 5,294,692 | 3/1994 | Barron et al. ........................... 526/301 |

FOREIGN PATENT DOCUMENTS

| 190892 | 8/1986 | European Pat. Off. . |
| 0 329 419 A2 | 8/1989 | European Pat. Off. . |
| 0 398 576 B1 | 11/1990 | European Pat. Off. . |
| 49-5512 | 4/1974 | Japan . |

OTHER PUBLICATIONS

J. A. Wenninger & G. N. McEwen, "International Cosmetic Ingredient Handbook", Third Edition, 1995.
K. G. Srinivasan and D. L. Neumann, "Cationic acrylic latex as paper saturants", Sep. 1986 Tappi Journal, pp. 104–106.
J. A. Wenniger & G. N. McEwen, "International Cosmetic Ingredient Handbook", Sixth Edition, 1995.

*Primary Examiner*—Judy M. Reddick
*Attorney, Agent, or Firm*—John D. Thallemer

[57] ABSTRACT

The present invention relates to thickened personal care compositions which utilize a thickening amount of an acrylate-based polymeric rheology modifier prepared by polymerization of a $C_1$–$C_6$ alkyl ester of acrylic acid and/or a $C_1$–$C_6$ alkyl ester of methacrylic acid, a monomer chosen from a vinyl-substituted heterocyclic compound containing at least one of a nitrogen or sulfur atom, (meth)acrylamide, a mono- or di-($C_1$–$C_4$)alkylamino ($C_1$–$C_4$)alkyl (meth)acrylate, a mono or di-($C_1$–$C_4$)alkylamino ($C_1$–$C_4$)alkyl (meth)acrylamide, and, optionally, an associative monomer.

2 Claims, No Drawings

6,025,431

THICKENED PERSONAL CARE COMPOSITION

This is a continuation-in-part application of pending U.S. patent application Ser. No. 08/698,690, filed on Aug. 16, 1996.

FIELD OF THE INVENTION

The present invention is related to personal care compositions which contain an acrylate-based, polymeric rheology modifier.

BACKGROUND OF THE INVENTION

Rheology modifiers are used generally to adjust or modify the rheological properties of aqueous compositions. Such properties include, without limitation, viscosity, flow rate, stability to viscosity change over time and the ability to suspend particles in such aqueous compositions. The particular type of modifier used will depend on the particular aqueous composition to be modified and on the particular end-use of that modified aqueous composition. Examples of conventional rheology modifiers include thickeners such as cellulosic derivatives, polyvinyl alcohol, sodium polyacrylate and other watersoluble macromolecules, and copolymeric emulsions in which monomers with acid groups have been introduced onto the main chain.

Another class of rheology modifiers known to thicken aqueous compositions is one typically referred to as associative modifiers. Such associative modifiers are reported in U.S. Pat. Nos. 4,743,698, 4,600,761, RE 33,156, 4,792,343, 4,384,096, 3,657,175, 5,102,936 and 5,294,692. As noted, these "alkali-swellable" thickeners become effective upon the addition of base, thereby raising the pH of the thickened composition to alkaline, but the thickeners do not thicken aqueous compositions having acidic pH. These types of thickeners also are believed to be incompatible in systems containing cationic ingredients.

Other rheology modifiers which are "activated" by the addition of acid to aqueous compositions which contain the modifiers also have been reported. As reported, emulsions are prepared via free-radical emulsion polymerization utilizing colloidal stabilizers. The emulsions are mixed with the composition to be thickened and then acid is added to the mix, thereby lowering the pH of the system to 6.5 to 0.5. These thickeners are reported to be effective at thickening certain acidic aqueous compositions, but are not effective at thickening aqueous compositions having basic pH.

It would be desirable to develop a polymeric rheology modifier which is stable to change in viscosity and phase separation over time when in the form of an emulsion, and which advantageously may be used to thicken both acidic and basic compositions.

SUMMARY OF THE INVENTION

The present invention is directed to personal care compositions which comprise at least one cosmetically-active agent in an amount effective to impart desired cosmetic properties to the personal care composition, and an acrylate-based polymeric rheology modifier in amounts effective to thicken the personal care composition compared to similar compositions which do not contain the polymeric rheology modifier.

DETAILED DESCRIPTION OF THE INVENTION

The present invention relates to personal care compositions which comprise a polymeric rheology modifier (PRM) which has been prepared by polymerizing from about 5 to about 80 weight percent of an acrylate monomer (a) selected from the group consisting of a $C_1$–$C_6$ alkyl ester of acrylic acid and a $C_1$–$C_6$ alkyl ester of methacrylic acid, from about 5 to about 80 weight percent of a monomer (b) selected from the group consisting of a vinyl-substituted heterocyclic compound containing at least one of a nitrogen or a sulfur atom, (meth)acrylamide, a mono- or di-($C_1$–$C_4$)alkylamino ($C_1$–$C_4$)alkyl (meth)acrylate and a mono or di-($C_1$–$C_4$) alkylamino ($C_1$–$C_4$)alkyl (meth)acrylamide, and 0 to about 30 weight percent of an associative monomer (c), all percentages based on the total weight of monomer used to prepare the PRM; and a cosmetically-active agent (CAA).

The PRM may be incorporated into the personal care composition in various forms, including powder, solution, dispersion and emulsion. Conventional methods of preparing acrylate-based polymers in the various forms are known readily by those skilled in the art of polymerization of acrylate-based polymers. Such methods include solution polymerization, precipitation polymerization and emulsion polymerization, for example. The PRM may be used to thicken aqueous personal care products such as creams and lotions and hair care products such as conditioners, shampoos, hair fixatives, gels, mousses, sprays and dyes.

While use of the PRMs of the present invention particularly is advantageous to thicken aqueous personal care compositions, the PRMs also may be used to thicken those personal care compositions which contain low amounts of water or no water. For instance, in personal care compositions where no water or very little water is present, the PRM may be dissolved or dispersed in solvents in which the PRM is soluble or dispersible and which conventionally are used in personal care compositions, and incorporated into the non-aqueous composition. The PRM may be dissolved or dispersed in the solvent either prior to formulation, in which case a solution or dispersion is added to other ingredients, or the PRM may be added in the form of a solid with other formulation ingredients and the solvent, thereby producing the thickened composition.

The PRMs of the present invention preferably are in the form of acrylate-based polymer emulsions which surprisingly have been found to be useful as PRMs for both acidic and basic pH aqueous compositions. The terms PRM and polymeric thickener are used interchangeably herein. In the most preferred form, the emulsions are stable, meaning that no appreciable phase separation or change in viscosity is noted over time, for example one to five days at standard temperature and pressure.

The acrylate monomers are selected from the group consisting of esters prepared from acrylic acid and $C_1$–$C_6$ alcohols, such as methyl, ethyl or propyl alcohol, and esters prepared from methacrylic acid and $C_1$–$C_6$ alcohols. Preferred acrylate monomers comprise $C_2$–$C_6$ alkyl esters of acrylic acid. Even more preferred, the acrylate monomer is ethyl acrylate. From about 5 to about 80 weight percent of the acrylate monomer are used in preparing the composition of the present invention, preferably from about 15 to about 70 weight percent, and more preferably, from about 40 to about 70 weight percent of the acrylate monomer are used, all percents based on total weight of monomer used to prepare the polymer.

Where stable aqueous emulsions of the PRMs are required, methyl acrylate may not be used in the present invention during preparation of the PRM, as it has been found to result in emulsions which are unstable with respect to viscosity change over time. It was unexpected that polymers prepared in the absence of a polymeric colloidal stabilizer with ethyl acrylate provided stability to viscosity change over time when compared to polymers prepared in the absence of a polymeric colloidal stabilizer with methyl acrylate, as emulsions prepared with methyl acrylate were found to be unstable to viscosity change.

In addition to the acrylate ester, polymerized therewith is a monomer selected from the group consisting of a vinyl-substituted heterocyclic compound containing at least one of a nitrogen or a sulfur atom, (meth)acrylamide, a mono- or di-$(C_1-C_4)$alkylamino $(C_1-C_4)$alkyl (meth)acrylate, a mono or di-$(C_1-C_4)$alkylamino $(C_1-C_4)$alkyl (meth)acrylamide. Exemplary monomers include N,N-dimethylamino ethyl methacrylate (DMAEMA), N,N-diethylamino ethyl acrylate, N,N-diethylamino ethyl methacrylate, N-t-butylamino ethyl acrylate, N-t-butylamino ethyl methacrylate, N,N-dimethylamino propyl acrylamide, N,N-dimethylamino propyl methacrylamide, N,N- diethylamino propyl acrylamide and N,N-diethylamino propyl methacrylamide. From about 5 to about 80 weight percent of the monomer are used in preparing the modifiers of the present invention, preferably from about 10 to about 70 weight percent, and more preferably, from about 20 to about 60 weight percent of the monomer are used, all percents based on total weight of monomer used to prepare the polymer.

Although the use of associative monomers is optional, in certain preferred embodiments, an associative monomer is used in amounts ranging from about 0.1 to about 30 weight percent, based on total weight of monomer used to prepare the polymer, in combination with the acrylate monomer and the monomer (b). When used, the associative monomers preferably are used at levels ranging from about 0.1 to about 10 weight percent. Such monomers include those disclosed in U.S. Pat. Nos. 3,657,175, 4,384,096, 4,616,074, 4,743,698, 4,792,343, 5,011,978, 5,102,936, 5,294,692, Re. 33,156, the contents of all which are hereby incorporated herein as if set forth in their entirety, and an allyl ether of the formula $CH_2=CR'CH_2OA_mB_nA_pR$ where R' is hydrogen or methyl, A is propyleneoxy or butyleneoxy, B is ethyleneoxy, n is zero or an integer, m and p are zero or an integer less than n, and R is a hydrophobic group of at least 8 carbon atoms. Preferred associative monomers include the urethane reaction products of a monoethylenically unsaturated isocyanate and non-ionic surfactants comprising $C_1-C_4$ alkoxy-terminated, block copolymers of 1,2-butylene oxide and 1,2-ethylene oxide, as disclosed in U.S. Pat. No. 5,294,692 (Barron et al.); an ethylenically unsaturated copolymerizable surfactant monomer obtained by condensing a nonionic surfactant with an α,β-ethylenically unsaturated carboxylic acid or the anhydride thereof, preferably a $C_3-C_4$ mono- or di-carboxylic acid or the anhydride thereof, more preferably a carboxylic acid or the anhydride thereof selected from the group consisting of acrylic acid, methacrylic acid, crotonic acid, maleic acid, maleic anhydride, itaconic acid and itaconic anhydride, as disclosed in U.S. Pat. No. 4,616,074 (Ruffner); a surfactant monomer selected from the urea reaction product of a monoethylenically unsaturated monoisocyanate with a nonionic surfactant having amine functionality as disclosed in U.S. Pat. No. 5,011,978 (Barron et al.); and a nonionic urethane monomer which is the urethane reaction product of a monohydric nonionic surfactant with a monoethylenically unsaturated monoisocyanate, preferably one lacking ester groups such as alpha, alpha-dimethyl-m-iso-propenyl benzyl isocyanate as disclosed in U.S. Pat. No. Re. 33,156 (Shay et al.). Particularly preferred are the ethylenically unsaturated copolymerizable surfactant monomers obtained by condensing a nonionic surfactant with itaconic acid. Methods for preparing such monomers are disclosed in detail in the various patents incorporated herein above.

In addition to the required and preferred monomers discussed above, monomers which provide cross-linking in the polymer also may be utilized in relatively low amounts, up to about 2 weight percent, based on the total weight of monomer used to prepare the polymer. When used, the cross-linking monomers preferably are used at levels of from about 0.1 to about 1 weight percent. Cross-linking monomers include multi-vinyl-substituted aromatic monomers, multi-vinyl-substituted alicyclic monomers, di-functional esters of phthalic acid, di-functional esters of methacrylic acid, multi-functional esters of acrylic acid, N-methylene-bis-acrylamide and multi-vinyl-substituted aliphatic monomers such as dienes, trienes, and tetraenes. Exemplary cross-linking monomers include divinylbenzene, trivinylbenzene, 1,2,4-trivinylcyclohexane, 1,5-hexadiene, 1,5,9-decatriene, 1,9-decadiene, 1,5-heptadiene, di-allyl phthalate, ethylene glycol dimethacrylate, polyethylene glycol dimethacrylate, penta- and tetra-acrylates, triallyl pentaerythritol, octaallyl sucrose, cycloparraffins, cycloolefins and N-methylene-bis-acrylamide. The polyethylene glycol dimethacrylates are particularly preferred for thickening in acid aqueous compositions, as they tend to minimize turbidity.

Preferred PRMs in emulsion form are prepared by forming an emulsion utilizing single-stage emulsion polymerization techniques. Monomer, water, free-radical initiator, surfactant in amounts effective to disperse the polymer in the water upon polymerization of the monomers, and from about 0.5 to about 20 weight percent of an alcohol selected from the group consisting of a $C_2-C_{12}$ linear or branched monohydric alcohol and a non-polymeric polyhydric alcohol, such as ethylene glycol, propylene glycol and glycerol, based on total weight of the emulsion, are combined in a polymerization reactor and maintained at a desired temperature and for a period of time which are effective to polymerize the monomers, thereby forming a polymeric emulsion comprising the copolymer of monomers (a) and (b), water, surfactant and alcohol.

The contents of the polymerization vessel preferably are maintained at a temperature and for a period of time effective to cause polymerization of the monomers. Preferably the polymerization reaction is initiated at about 30 degrees centigrade, with the contents of the polymerization vessel attaining a temperature of about 60 degrees centigrade. The reaction time will be from about 1 to about 6 hours. One skilled in the art of emulsion polymerization will be able to ascertain readily exactly what conditions of temperature and time are required, as both are well within the knowledge of one skilled in the art.

Preferably, from about 1 to about 10 weight percent of the alcohol are used and, more preferably, from about 1 to about 5 weight percent of the alcohol are used, based on the total weight of the emulsion. If no alcohol, or an insufficient amounts of the alcohol, is used in preparing the emulsion, the resultant emulsion will not be stable to change in viscosity over time. It is desirable to minimize the level of alcohol used. The maximum amount of alcohol used may be limited practically by factors such as cost, flammability and volatile organic compound environmental concerns. Other than those factors, amounts of alcohol in excess of 20 weight percent conceivably may used.

Where stable emulsions are required, it is essential that polymeric colloidal stabilizers such as polyvinyl alcohol not be used during preparation of the emulsion via emulsion polymerization in any amount which materially alters the properties of the emulsion, particularly the emulsion stability. Preferably, no polymeric colloidal stabilizer is used during emulsion preparation. It was discovered surprisingly that use of such polymeric colloidal stabilizers results in emulsions which are not stable to changes in viscosity or phase separation over time. Accordingly, the emulsions and rheology modifiers comprising the emulsions essentially are free and more preferably are free of polymeric colloidal stabilizers.

CAA, as used herein, means any material, composition or compound applied to the body, typically to the skin, hair, or nails, for the cosmetic treatment thereof. Exemplary agents include emollients and lubricants for softening or smoothing, surfactants for cleansing and other purposes, natural or synthetic polymers for the topical coating of the hair to build body or to enhance setting characteristics, hair conditioning agents, and the like. Such CAAs include, without limitation mineral oils, glycerin, beeswax, lanolin, acetylated lanolin, stearic acid, palmitic acid, cetyl alcohol, sodium lauryl sulfate, sodium salts of olefin sulfonates, various proteins, polymeric sugars, conditioning agents such as polyquaterniun 7, polyquaterniun 4, polyquaterniun 10, and polyquaterniun 11, and hair fixative resins such as Acrylates/PVP copolymer, Acrylates/Octylacrylamide copolymer, Acrylates copolymer and Acrylates/Acrylamide copolymer, Acrylates/VA copolymer, Acrylamide/Acrylates/DMAPA/Methoxy PEG Methacrylate copolymer. This list is intended to exemplitive only and not limiting as to the materials that are encompassed by the term cosmetically-active agent.

In water-based personal care compositions, the water is a vehicle for application to some part of the body of some CAA that will have a cosmetic effect of some type, whether such effect is a softening or cleansing or strengthening or body enhancing effect. It is the intent here to include within the term CAA any and all of such materials that are provided for cosmetic effect. The personal care compositions of the present invention can also include combinations of CAAs of various types, coloring agents, fragrances, preservatives, and the like. The levels at which the CAAs are used are conventional and are known to those skilled in the art of personal care compositions.

The present invention also provides a method of preparing a thickened personal care composition comprising combining the PRM of the present invention in amounts effective to increase the viscosity of the personal care composition compared to a similar composition which does not contain the PRM, and at least one CAA, thereby producing a thickened personal care composition.

The polymeric rheology modifier may be incorporated into the personal care composition at the time the composition is formulated, or the PRM may be post-added to an already-formulated personal care composition. When incorporated during preparation of the personal care composition, the PRM may be combined with water or other solvent in which the PRM either is soluble or dispersible, the CAA and other ingredients as needed and/or desired, for example emulsifiers. When used in the form of a stable emulsion, the emulsion may be combined with the CAA and other ingredients upon formulation, or the emulsion may be post-added and blended with compositions which have been formulated previously.

Preferably, as little of the PRM as possible is used in preparing the personal care compositions of the present invention, with the minimum amount allowed being an amount effective to thicken the personal care composition. The amount of PRM required to effectively thicken the personal care composition will depend upon the particular polymer and particular personal care composition. Typically, the thickened personal care composition will contain from about 0.1 to about 10 dry weight percent of the PRM, based on the total weight of the thickened personal care composition. Preferably, the thickened personal care composition will contain from about 0.5 to about 5 dry weight percent of the PRM.

The PRMs meet a number of needs of personal care product formulators, such as compatibility with cationic ingredients, thickening efficiency, clarity in gels, pH versatility (i.e. ability to thicken over wide acidicalkaline pH range), and tolerance to salts. A number of examples detailing personal care compositions making use of the PRMs of the present invention have been evaluated and are summarized below. These examples include both hair care and skin care applications, as the PRMs appear to offer benefits in both areas.

The following examples are set forth to exemplify the invention and should not be used to limit the scope of the invention, which scope is set forth in the claims appended hereto.

Three PRMs of the present invention were prepared via the emulsion polymerization methods described herein above. These PRMs are designated PRM 1A, 1B and 1C, respectively. The monomeric composition for each PRM is set forth in Table 1. PRMs 1B and 1C were prepared utilizing an associative monomer, while PRM 1A did not utilize an associative monomer.

TABLE 1

| | monomer[1] | | |
|---|---|---|---|
| | 1A | 1B | 1C |
| ethyl acrylate | 60 | 57 | 60 |
| dimethylaminoethyl methacrylate | 40 | 38 | 37 |
| associative monomer | — | 5[2] | 3[3] |

[1] = All values are in weight percent, based on total weight of monomer used to prepare the PRM
[2] = ceteth-20 itaconate
[3] = ceteth-20 allyl ether The thickening efficiency of each PRM was evaluated by measuring viscosity build in prototype personal care formulations. Viscosity was measured using a Brookfield RVF heliopath viscometer at 10 rpm. All viscosity values are reported in units of centipoise (cps). Initial viscosity measurements were taken after the personal care compositions were formulated and allowed to equilibrate under ambient temperature and pressure for 24 hours. Eight and/or seven day viscosities were measured 8 or 7 days, respectively, after the initial viscosity was measured. In all cases, viscosities of the formulations containing the PRM were compared to viscosities of a control which contained no PRM. The formulations evaluated are detailed in Formulations 1 through 9, below. Evaluations also were conducted on model systems to determine stability to bleach, e.g. peroxide. Peroxide stability was determined by boiling a 1% solids, 6% $H_2O_2$ solution (pH adjusted to 3 using $H_3PO_4$) for a total of 20 hours. Results are reported as % $H_2O_2$ retained.

Results and Discussion

The PRMs are useful in a broad range of personal care products. The examples shown here highlight their effectiveness at building viscosity in diverse formulations, including cationic alpha hydroxy acid (AHA) creams, antiperspirant lotions, hair conditioners, specialty shampoos, hair and skin gels, and hair dyes. All PRMs evaluated were effective at raising the viscosity of personal care prototypes in hair and skin care systems.

AHA Creams

Performance of the PRMs was evaluated in the AHA cream set forth in Formulation 1. This emulsion is low in pH and contains cationic surfactants. The PRMs surprisingly exhibit both cationic compatibility and acid thickening. Results are set forth in Table 2.

TABLE 2

| PRM | pH | Initial viscosity (cps) | Day 8 viscosity (cps) | % of Day 8 control viscosity |
|---|---|---|---|---|
| 1A | 2.1 | 6,438 | 11,219 | 151 |
| 1B | 2.2 | 37,000 | 28,563 | 384 |
| none[(1)] | 2.1 | 10,344 | 7,438 | 100 |
| 1C | 2.6 | 24,625 | 26,625 | 428 |
| none[(2)] | 2.4 | 5,570 | 9,563 | 100 |

[(1)] and [(2)]; PRMs 1A and 1B were tested simultaneously against the same control, while PRM 1C was tested at a later time against a second, but similar, control independently of PRMs 1A and 1B.

As clearly is seen, the addition of only 0.5% solids PRM is effective at raising the viscosity of a cationic AHA cream in comparison to a cream without the PRM.

Antiperspirant Lotion

Performance of each PRM was evaluated in the aqueous antiperspirant lotion set forth in Formulation 2. This low pH emulsion contains a high level of electrolyte as aluminum chlorohydrate. Therefore, the PRM exhibits salt tolerance as well as low pH viscosity build. Results are set forth in Table 3.

TABLE 3

| PRM | pH | Day 7 viscosity (cps) | % of Day 7 control viscosity |
|---|---|---|---|
| 1A | 4.1 | 2,888 | 74 |
| 1B | 4.1 | 20,650 | 529 |
| none[(1)] | 4.0 | 3,900 | 100 |
| 1C | 4.3 | 3,325 | N/A |
| none[(2)] | 4.1 | phase separation | N/A |

[(1)] and [(2)]; PRMs 1A and 1B were tested simultaneously against the same control, while PRM 1C was tested at a later time against a second, but similar, control independently of PRMs 1A and 1B.
Control[(2)] formed an unstable emulsion, i.e. there was phase separation, which prevented determination of a viscosity for the control formulation.

As is clearly seen, only 1.0% solids of the associative PRM is effective at significantly raising the viscosity of an aqueous, high salt antiperspirant lotion in comparison to a product without the PRM.

Hair Conditioner PRMs 1A and 1B were evaluated in the rinse-off hair conditioner set forth in Formulation 3. This formulation contains a high loading of both monomeric and polymeric conditioning agents. The unexpected, excellent viscosity build shown in Table 4 exhibits the surprising ability of the PRMs to build viscosity of aqueous, cationic-rich formulations at a 2% solids level.

TABLE 4

| PRM | pH | initial viscosity (cps) | % of control viscosity |
|---|---|---|---|
| 1A | 4.4 | 5,288 | 1,763 |
| 1B | 4.3 | 18,488 | 6,163 |
| none | 4.4 | 300 | 100 |

Shampoos

These PRMs were formulated into the conditioning shampoo prototype set forth in Formulation 4. As is seen in Table 5, PRMs 1A and 1B were effective equally at building viscosity of the shampoo after mixing. Thus, the PRMs are shown to be capable of boosting viscosity of highly concentrated surfactant systems.

TABLE 5

| PRM | pH | initial viscosity | % of control viscosity |
|---|---|---|---|
| 1A | 5.9 | 51,656 | 1,223 |
| 1B | 6.0 | 54,000 | 1,278 |
| none | 6.0 | 4,225 | 100 |

Additional work was performed to demonstrate the ability of the PRMs to build viscosity of highly concentrated surfactant systems. The PRMs were post-added as a 20% polymer solids aqueous emulsion to three commercial shampoos which were purchased and evaluated. The shampoos include a mild baby shampoo available from Johnson & Johnson, Rave® moisturizing shampoo, available from Chesebrough-Pond's USA Company, and Prell® shampoo, available from Procter and Gamble. The ingredients in these products, as reported on the label, are listed in Formulations 5, 6 and 7. While the exact levels of use of the particular ingredients contained in the respective commercial shampoos may be proprietary, ranges of the levels of such ingredients used by those skilled in the art are conventional and known by those skilled in the art of formulating personal care compositions. As is seen in the results reported in Table 6, the PRMs are effective at building viscosity in all cases.

TABLE 6

| formulation | formulation pH | PRM | initial viscosity (cps) | % of control viscosity |
|---|---|---|---|---|
| Johnson's | 7.8 | 1A | 17,344 | 2,313 |
| Johnson's | 7.8 | 1B | 21,469 | 2,863 |
| Johnson's | 7.9 | 1C | 17,375 | 2,317 |
| Johnson's | 6,6 | none | 750 | 100 |
| Rave | 8.8 | 1A | 21,906 | 8,762 |
| Rave | 8.9 | 1B | 26,344 | 10,538 |
| Rave | 8.9 | 1C | 17,938 | 7,175 |
| Rave | 5.66 | none | 250 | 100 |
| Prell | 8.0 | 1A | 28,000 | 1,244 |
| Prell | 7.9 | 1B | 30,844 | 1,371 |
| Prell | 8.0 | 1C | 18,781 | 835 |
| Prell | 6.6 | none | 2,250 | 100 |

Gels

Clarity is an important attribute for many hair and skin care gels. Using existing thickener technology, low pH lotions or conditioning gels with adequate viscosity typically cannot be made clear because commercial clear thickeners are incompatible with the low pH and/or cationics, and emulsions are necessary. PRMs 1B and 1C were used to thicken two clear AHA gels, as set forth in Formulation 9, one of which contains an additional conditioner (polyquaternium-4) and one of which does not. The viscosity results, which are shown in Table 7, demonstrate that the PRMs efficiently build viscosity of clear gels.

TABLE 7

| formulation | PRM | initial viscosity (cps) |
|---|---|---|
| + conditioner | 1B | 23,344 |
| − conditioner | 1B | 24,594 |
| control[(1)] | none | <100 |
| + conditioner | 1C | 21,063 |
| − conditioner | 1C | 20,594 |
| control[(2)] | none | <250 |

[(1)] and [(2)]: PRMs 1B and 1C were tested independent of one another against separate controls.

Hair Dyes

Hair dye systems typically are highly alkaline during use. The PRM is found to be effective at building the viscosity of a two component permanent hair dye after the two components are blended. This is true both when the polymer is delivered in the acidic developer or in the alkaline dye base. The results set forth in Table 8 clearly show PRM 1B is effective at boosting the viscosity of the Nice 'n Easy® commercial hair dye product available from Clairol Inc, the composition of which is set forth in Formulation 9.

TABLE 8

| PRM | Delivery | pH of blend | viscosity after blending |
|---|---|---|---|
| 1B | polymer from developer | 9.7 | 5,200 |
| 1B | polymer from dye base | 9.7 | 4,713 |
| none[(1)] | | 9.7 | 2,900 |
| 1C | polymer from developer | 9.6 | 4,500 |
| 1C | polymer from dye base | 9.6 | 3,250 |
| none[(2)] | | 9.6 | 1,900 |

[(1)] and [(2)]: PRMs 1B and 1C were tested independent of one another against separate controls.

Peroxide Stability

Compatibility with hydrogen peroxide can be an important attribute in certain personal care applications, such as hair dyes. A standard screening test for peroxide compatibility is a 20 hour boil test. Peroxide concentration is measured before and after a 20 hour boil regime. Retention of more than 92% of the initial peroxide concentration is usually indicative of a product which will exhibit satisfactory shelf stability. PRMs 1A and 1B were evaluated in such a test at 1% solids using 6% hydrogen peroxide, with the pH adjusted to 3 with $H_3PO_4$. The results are summarized in Table 9.

TABLE 9

| PRM | % peroxide retained |
|---|---|
| 1A | 98 |
| 1B | 99 |

These results show that these PRMs exhibit excellent peroxide compatibility.

The PRMs appear to show much promise in personal care applications. They build viscosity in the presence of such common personal care ingredients as cationics, acids, bases, salts and surfactants. Viscosities of such diverse hair and skin formulations as creams, lotions, antiperspirants, hair conditioners, specialty shampoos, mousses, hair and skin gels, and hair dyes are enhanced by relatively low concentrations of these polymers. Furthermore, behaviors of interest for personal care, such as pseudoplastic flow, are evident with these polymers.

| ingredient | wt. % |
|---|---|
| Formulation 1 Cationic AHA Lotion | |
| PRM | 0.50 (solids) |
| propylene glycol | 2.00 |
| Na$_4$EDTA (39%) | 0.25 |
| octyl methoxycinnamate | 4.00 |
| lapyrium chloride | 0.50 |
| steapyrium chloride | 0.50 |
| cetearyl alcohol | 2.00 |
| glyceryl stearate/glycerin | 3.00 |
| cyclomethicone | 4.00 |
| dimethicone | 1.00 |
| isopropyl myristate | 2.00 |
| glycolic acid (70%) | 4.29 |
| water | to 100% |
| Formulation 2 Aqueous Antiperspirant Lotion | |
| PRM | 1.00 (solids) |
| propylene glycol | 4.00 |
| aluminum chlorohydrate (50%) | 42.00 |
| glyceryl stearate/PEG-100 stearate | 3.00 |
| cetearyl alcohol | 0.75 |
| glyceryl stearate/glycerine | 1.50 |
| cyclomethicone | 2.00 |
| water | to 100% |
| Formulation 3 Rinse-off Hair Conditioner | |
| PRM | 2.00 (solids) |
| polyquaternium-10 | 0.50 |
| glycerin | 2.00 |
| laneth-15 | 1.00 |
| cetearyl alcohol | 2.50 |
| mineral oil | 2.00 |
| cetyl acetate/acetylated lanolin alcohol | 1.00 |
| cetrimonium chloride (25%) | 4.00 |
| citric acid (20%) | to pH 4 |
| water | to 100% |
| Formulation 4 Conditioning Shampoo | |
| PRM | 2.00 (solids) |
| polyquaternium-10 | 0.75 |
| sodium lauryl sulfate (29%) | 17.00 |
| sodium laureth sulfate (26%) | 13.00 |
| cocamidopropyl betaine (35%) | 2.50 |
| cocamide DEA | 4.50 |
| ethylene glycol distearate | 1.25 |
| steareth-20 | 0.30 |
| dimethicone | 3.00 |
| citric acid | to pH 6 |
| water | to 100% |
| Formulation 5 Johnson & Johnson Baby Shampoo | |
| PRM | 2.50 (solids) |
| Water | |
| PEG-80 sorbitan laurate | |
| Cocamidopropyl betaine | |
| Sodium trideceth sulfate | |
| Glycerin | |
| Lauroamphoglycinate | |
| PEG-150 distearate | |
| Sodium laureth-13 carboxylate | |
| Fragrance | |
| Polyquaternium-10 | |
| Tetrasodium EDTA | |
| Quaternium-15 | |
| Citric acid | |
| D&C yellow #10 | |
| D&C orange #4 | |

-continued

Formulation 6
Rave ® Moisturizing Shampoo

| | |
|---|---|
| PRM | 2.50 (solids) |

Water
Sodium lauryl sulfate
Cocamidopropyl betaine
Sodium chloride
Polyquaternium-10
Glycerin
Polyquaternium-7
Oleth-3 phosphate
Fragrance
BHT
Tetrasodium EDTA
DMDM hydantoin
Iodopropynyl butyl carbamate
Red 33
Yellow 5

Formulation 7
Prell ® Shampoo

| | |
|---|---|
| PRM | 2.50 (solids) |

Water
Ammonium laureth sulfate
Ammonium lauryl sulfate
Cocamide DEA
Ammonium xylenesulfonate
Sodium phosphate
Fragrance
Disodium phosphate
Sodium chloride
EDTA
Benzophenone-2
Methylchloroisothiazolinone
Methylisothiazolinone
D&C Green No. 8
FD&C Blue No. 1

Formulation 8
Conditioning Gel

| ingredient | wt. % | wt. % | wt. % |
|---|---|---|---|
| glycolic acid (70%) | 4.29 | 4.29 | 4.29 |
| PRM | 3.00 | 3.00 | — |
| polyquaternium-4 | 0.50 | — | — |
| water | to 100% | to 100% | to 100% |

Formulation 9
Nice 'n Easy ® Dye Ingredients
Natural Dark Brown #120

| ingredient | wt. % |
|---|---|
| PRM | 3.0 (solids) |

Dye base water
oleic acid
propylene glycol
isopropyl alcohol
nonoxynol-2
nonoxynol-4
ethoxydiglycol
ammonium hydroxide
cocamide DEA
PEG-8 hydrogenated tallow amine
sulfated castor oil
sodium sulfite
erythorbic acid
fragrance
EDTA
resorcinol
p-phenylenediamine
1-naphthol
N,N-bis(2-hydroxyethyl)-p-phenylenediamine sulfate -continued Developer water
hydrogen peroxide
nonoxynol-9
nonoxynol-4
phosphoric acid
cetyl alcohol
stearyl alcohol

We claim:

1. A personal care composition comprising a polymeric rheology modifier and a cosmetically-active agent, wherein said polymeric rheology modifier is compatible with cationically charged ingredients of personal care compositions and is prepared by polymerization of monomers consisting of 5 to 80 weight percent of an acrylate monomer (a) selected from the group consisting of a $C_1$–$C_6$ alkyl ester of acrylic acid and a $C_1$–$C_6$ alkyl ester of methacrylic acid;

5 to 80 weight percent of a monomer (b) selected from the group consisting of a vinyl-substituted heterocyclic compound containing at least one of a nitrogen or sulfur atom, (meth)acrylamide, a mono- or di-($C_1$–$C_4$) alkylamino ($C_1$–$C_4$)alkyl (meth)acrylate, and a mono or di-($C_1$–$C_4$)alkylamino ($C_1$–$C_4$)alkyl (meth) acrylamide;

0.1 to 30 weight percent of an associative monomer (c) which is selected from the group consisting of urethane reaction products of a monoethylenically unsaturated isocyanate and non-ionic surfactants comprising $C_1$–$C_4$ alkoxy-terminated, block copolymers of 1,2-butylene oxide and 1,2-ethylene oxide, an ethylenically unsaturated copolymerizable surfactant monomer obtained by condensing a nonionic surfactant with an $\alpha,\beta$-ethylenically unsaturated carboxylic acid or the anhydride thereof, a surfactant monomer selected from the group consisting of urea reaction product of a monoethylenically unsaturated monoisocyanate with a nonionic surfactant having amine functionality, an allyl ether of the formula $CH_2{=}CR'CH_2OA_mB_nA_pR$ where R' is hydrogen or methyl, A ispropyleneoxy or butyleneoxy, B is ethyleneoxy, n is zero or an integer, m and p are zero or an integer less than n, and R is a hydrophobic group of at least 8 carbon atoms, and a nonionic urethane monomer which is the urethane reaction product of a monohydric nonionic surfactant with a monoethylenically unsaturated isocyanate, wherein the percentage of monomers is based on 100 weight percent; and a cosmetically-active agent in an amount effective to impart cosmetic properties to the personal care composition.

2. The personal care composition according to claim 1 wherein monomer (b) of the polymeric rheology modifier is selected from the group consisting of N,N-dimethylamino ethyl methacrylate, N,N-diethylamino ethyl acrylate, N,N-diethylamino ethyl methacrylate, N-t-butylamino ethyl acrylate, N-t-butylamino ethyl methacrylate, N,N-dimethylamino propyl acrylamide, N,N-dimethylamino propyl methacrylamide, N,N-diethylamino propyl acrylamide and N,N-diethylamino propyl methacrylamide.

* * * * *